United States Patent
Abdalla

(10) Patent No.: US 11,332,439 B2
(45) Date of Patent: May 17, 2022

(54) ANTHOCYANIN COMPLEX SYNTHESIZED FROM DATE PALM LEAF EXTRACT

(71) Applicant: UNITED ARAB EMIRATES UNIVERSITY, Al Ain (AE)

(72) Inventor: Hassan Mohamed Hassan Abdalla, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/070,379

(22) Filed: Oct. 14, 2020

(65) Prior Publication Data

US 2022/0112161 A1    Apr. 14, 2022

(51) Int. Cl.
| | |
|---|---|
| *C07C 403/24* | (2006.01) |
| *C09B 61/00* | (2006.01) |
| *A23L 5/43* | (2016.01) |
| *A23L 5/44* | (2016.01) |

(52) U.S. Cl.
CPC .............. *C07C 403/24* (2013.01); *A23L 5/44* (2016.08); *C09B 61/00* (2013.01); *A23L 5/43* (2016.08)

(58) Field of Classification Search
CPC . C07C 403/24; A23L 5/44; A23L 5/43; C09B 61/00
See application file for complete search history.

(56) References Cited

U.S. PATENT DOCUMENTS

| | | |
|---|---|---|
| 7,119,238 B2 | 10/2006 | Khachik |
| 2002/0055471 A1 | 5/2002 | Bailey et al. |
| 2006/0106136 A1 | 5/2006 | Abu-Sharkh |

(Continued)

FOREIGN PATENT DOCUMENTS

| | | |
|---|---|---|
| CN | 101167623 A | 4/2008 |
| DE | 2459226 A1 | 6/1976 |
| WO | 2009008697 A1 | 1/2009 |

OTHER PUBLICATIONS

Umoren et al. Date palm (*Phoenix dactylifera*) leaf extract as an eco-friendly corrosion inhibitor for carbon steel in 1M hydrochloric acid solution Anti-Corrosion Methods and Materials 62/1 (2015) 19-28 (Year: 2015).*

(Continued)

*Primary Examiner* — Subbalakshmi Prakash
(74) *Attorney, Agent, or Firm* — Nath, Goldberg & Meyer; Richard C. Litman

(57) ABSTRACT

The anthocyanin synthesized from date palm may include co-pigmented anthocyanin complexes synthesized by extracting an anthocyanin from date palm leaves and reacting the anthocyanin with phenolic compounds also resulting from date palm leaf extraction in order to produce a co-pigmented anthocyanin complex. Date palm leaf powder may be mixed with water containing about 1.08% hydrochloric acid in a glass or ceramic lined reactor, and extraction may be performed by boiling the mixture for an hour or more. The color of the co-pigmented anthocyanin complex produced by this method may be adjusted by continuing the heating in half hour increments, in order to deepen the hue of the co-pigmented anthocyanin complex. The co-pigmented anthocyanin complex may be separated from the liquid mixture by first filtering the liquid mixture, refining the liquid mixture by adding gelatin to form a colloidal solution, and freeze-drying the refined liquid mixture.

2 Claims, 9 Drawing Sheets

(56) References Cited

U.S. PATENT DOCUMENTS

2016/0278416 A1     9/2016    Muhamad et al.
2020/0017690 A1*    1/2020    Norddahl ................ C09B 61/00

OTHER PUBLICATIONS

Hakker et al. CH 715658 B1, Jun. 30, 2020 machine translation (Year: 2020).*

"Natural Green Food Coloring—Fresh Spinach Leaves," Apr. 26, 2018, Sew Historically website, printed Sep. 28, 2020.

Mohamed et al., "A noval Natural Food Colorant and Plant growth biostimulant from Date Palm Leaves Date Palm Leaves Waste as Resource," Expo 2020 Dubai, May 29, 2019. Accessible at: http://focusky.com/utsp/akwe/.

Kriaa et al., "Phenolic Contents and Antioxidant Activities of Date Palm (*Phoenix dactylifera* L.) Leaves", International Journal of Food Properties (2012), vol. 15, pp. 1220-1232.

Al-Haj-Ali et al., "Thermodynamics and Kinetics of Inhibition of Aluminum in Hydrochloric Acid by Date Palm Leaf Extract", J. Appl. Sci. Environ. Manage. (2014), vol. 18, Iss. 3, pp. 543-551.

Mainasara et al., "Antibacterial Activity and Nutritional Content of Fresh and Dried Date Fruits (*Phoenix dactylifera*) L", International Joural of Science and Healthcare Research (2017), vol. 2, Iss. 1, pp. 15-20.

Khoo et al., "Anthocyanidins and anthocyanins: colored pigments as food, pharmaceutical ingredients, and the potential health benefits", Food and Nutrition Research (2017), vol. 61, pp. 1-21.

Alfaro-Viquez et al., "An extract from date palm fruit (*Phoenix dactylifera*) acts as a co-agonist ligand for the nuclear receptor FXR and differentially modulates FXR target-gene expression in vitro", PLoS ONE (2018), vol. 13, No. 1, 23 pages.

\* cited by examiner

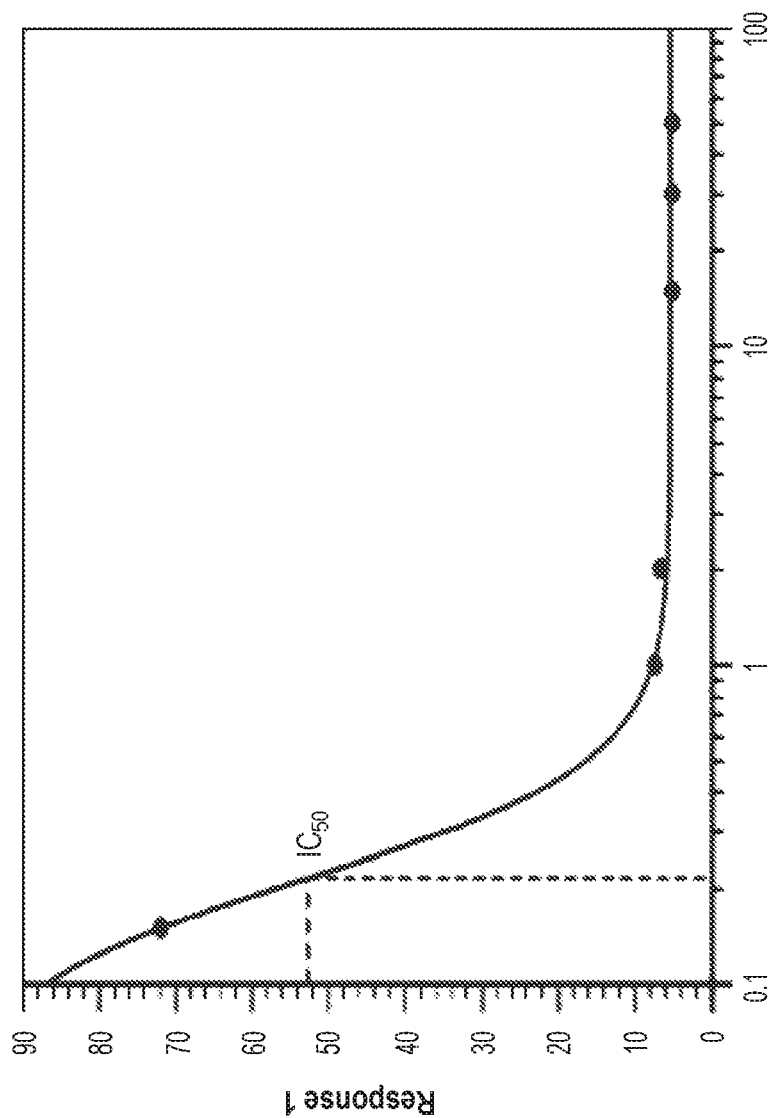

ANTHOCYANIN COMPLEX SYNTHESIZED FROM DATE PALM LEAF EXTRACT

BACKGROUND

1. Field

The disclosure of the present patent application relates to food colorants, and particularly to an anthocyanin synthesized from date palm and the method of synthesizing the anthocyanin by extraction from date palm leaves.

2. Description of the Related Art

In general, phytochemicals (such as phenolics, carotenoids, sterols, alkaloids, and anthocyanins) are extracted from natural sources using organic solvents. However, these methods frequently require either expensive, time-consuming steps to remove all traces of the organic solvents and separate the individual phytochemicals, or may result in a contaminated extract containing trace amounts of organic solvents or a mixture of desired and undesired phytochemicals.

Recent work has focused on developing environmentally friendly, cost-effective methods of extraction, including supercritical fluid extraction (SFE), microwave extraction (MWE), pulsed electric field (PEF), high-pressure processing (HPP), ultrasonic extraction (UE), and ohmic heating (OH). These approaches generally avoid issues with thermal degradation and provide easier separation without the risk of retaining residual organic solvents. However, these approaches must be optimized for individual plant compositions, as minor variations in pre-treatment materials and extraction conditions can vary significantly based upon the specific plant composition and desired phytochemical.

Anthocyanins are water-soluble compounds having polyphenolic structures that provide a degree of hydrophobic character. As a result of their polyphenolic structures, anthocyanins are also soluble in organic solvents. The combination of both polar and hydrophobic regions makes anthocyanins particularly difficult to extract.

Thus, an anthocyanin synthesized from date palm solving the aforementioned problems is desired.

SUMMARY

The anthocyanin synthesized from date palm may be obtained by extracting an anthocyanin from date palm leaves and reacting the anthocyanin with phenolic compounds also extracted from the date palm leaves in order to produce a co-pigmented anthocyanin complex. The anthocyanin may be extracted by collecting date palm (*Phoenix dactylifera*) leaves, shredding and grinding the date palm leaves to obtain date palm leaf powder, mixing the date palm leaf powder with water containing about 1.08% hydrochloric acid (100-150 g date palm leaf powder per liter) in a glass or ceramic lined reactor, and extracting anthocyanins from the date palm leaves by boiling the mixture for an hour until the mixture turns red, indicating the successful extraction of the anthocyanins and their combination with phenolic compounds also extracted from the date palm leaf powder. The color of the co-pigmented anthocyanin complex produced by this method may be adjusted by continuing the heating in half-hour increments in order to deepen the hue of the co-pigmented anthocyanin complex. The co-pigmented anthocyanin complex may be separated from the liquid mixture by first filtering the liquid mixture, refining the liquid mixture by adding gelatin to remove the salt, and freeze-drying the refined liquid mixture.

The co-pigmented anthocyanin complex synthesized from date palm leaves may be useful as a food colorant, nutritional supplement, or anti-oxidant additive to food, pharmaceuticals, beverages, or the like.

These and other features of the present subject matter will become readily apparent upon further review of the following specification.

BRIEF DESCRIPTION OF THE DRAWINGS

FIG. 6B is a plot of the reaction kinetics of the anthocyanin synthesized from date palm against DPPH free radical.

Similar reference characters denote corresponding features consistently throughout the attached drawings.

DETAILED DESCRIPTION OF THE PREFERRED EMBODIMENTS

The anthocyanin synthesized from date palm may be obtained by extracting an anthocyanin from date palm leaves and reacting the anthocyanin with phenolic compounds also extracted from date palm leaves in order to produce a co-pigmented anthocyanin complex. The anthocyanin may be extracted by collecting date palm (*Phoenix dactylifera*) leaves, shredding and grinding the date palm leaves to obtain date palm leaf powder, mixing the date palm leaf powder with water containing about 1.08% hydrochloric acid (100-150 g date palm leaf powder per liter) in a glass or ceramic-lined reactor, and extracting anthocyanins from the date palm leaves by boiling the mixture for an hour until the mixture turns red, indicating the successful extraction of the anthocyanins and their combination with phenolic compounds also extracted from the date palm leaf powder. The color of the co-pigmented anthocyanin complex produced by this method may be adjusted by continuing the heating in half-hour increments in order to deepen the hue of the co-pigmented anthocyanin complex. The co-pigmented anthocyanin complex may be separated from the liquid mixture by first filtering the liquid mixture, refining the liquid mixture by adding gelatin to remove the salt, and freeze-drying the refined liquid mixture.

The co-pigmented anthocyanin complex synthesized from date palm leaves may be useful as a food colorant, nutritional supplement, or anti-oxidant additive to food, pharmaceuticals, beverages, or the like.

The term "about", when used herein to modify a numerical value, shall mean within 10% of that numerical value.

Figure 7:
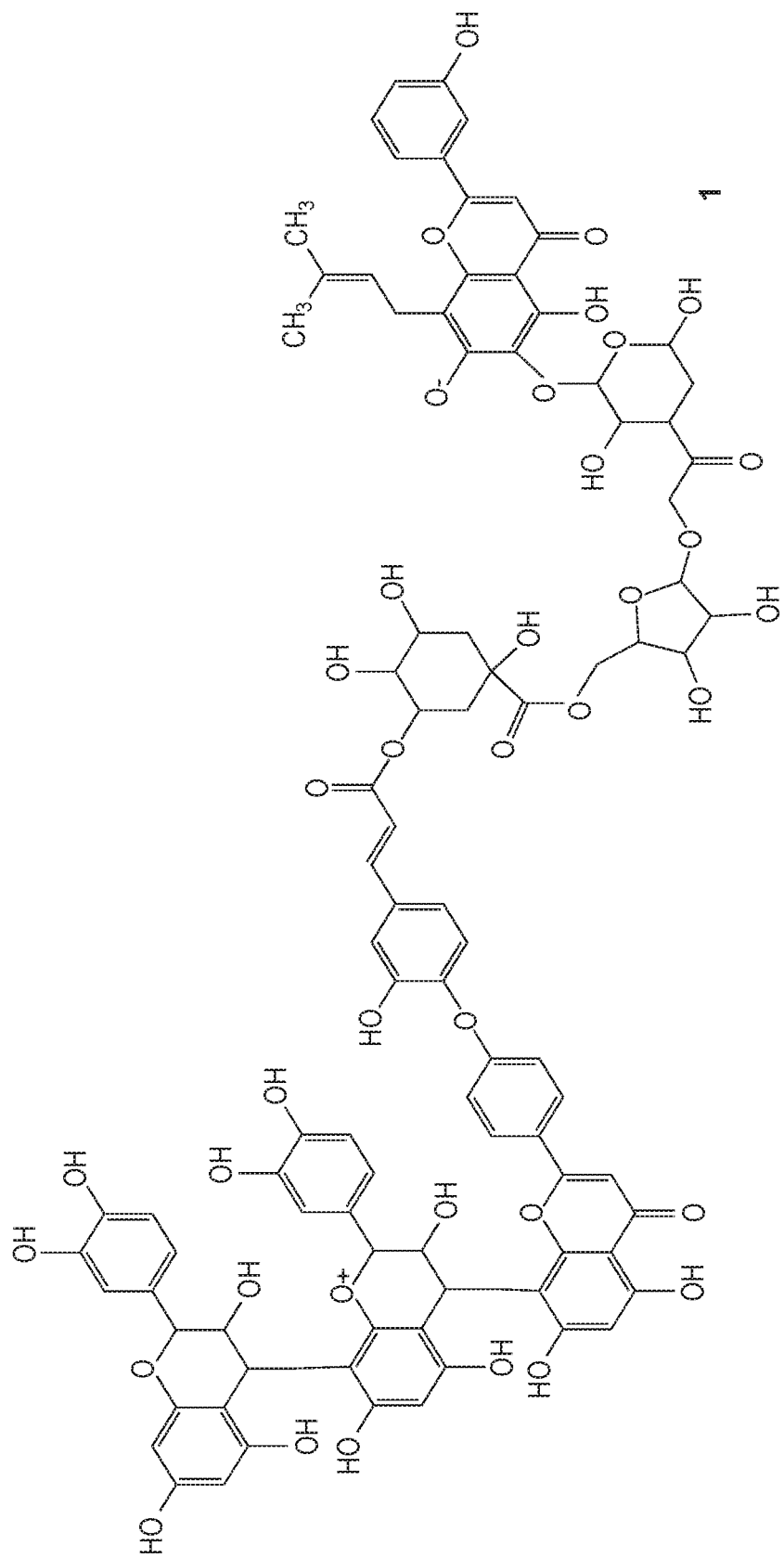
FIG. 7 is the proposed structural formula of the anthocyanin synthesized from date palm.

The co-pigmented anthocyanin complex may comprise the compound $C_{93}H_{83}O_{39}$. In an embodiment, the co-pigmented anthocyanin complex may comprise the structure of compound 1, shown below and also in FIG. 7.

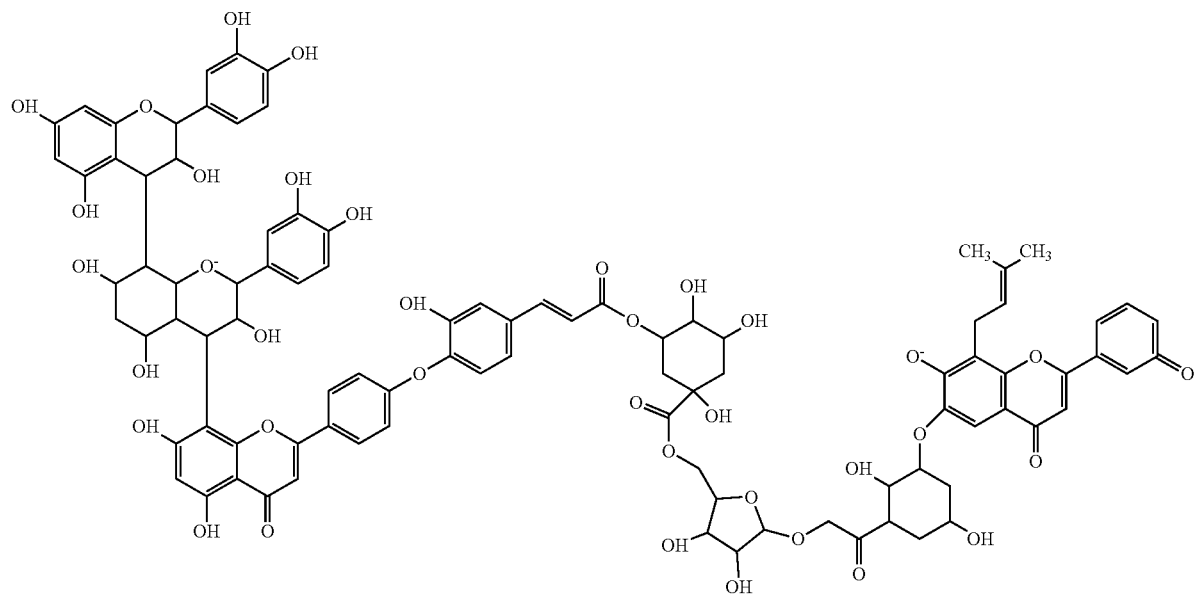

The anthocyanin synthesized using date palm may be co-pigmented. Co-pigmentation involves the enhancement of anthocyanin pigmentation by non-covalent linkage of the anthocyanin to one or more colorless flavonoids, or co-pigments. Flavonoids are polyphenolic secondary metabolites commonly found in plants or fungi. The flavonoids themselves are colorless. However, when complexed to the anthocyanin they may enhance and/or modify the pigmentation of the anthocyanin. Thus, the co-pigmented anthocyanin complex may result from linkages formed between the anthocyanins isolated from the date palm leaves and colorless flavonoids also found in date palm leaf extract.

The anthocyanin synthesized using date palm will be better understood with reference to the following examples.

Example 1

Synthesis of an Anthocyanin Using Date Palm

Green leaves were removed from waste date palm fronds and cut into about 1 cm long pieces. The date palm leaf pieces were then ground using a cutting mill and about 500 g of ground leaves were added to about 3 liters of water containing ionic liquid (hydrochloric acid, about 1.08% [w/vol] hydrochloric acid [100-150 g/L of water]) and boiled for an hour. The solution turned red, confirming co-pigmentation of the anthocyanin with flavonoids also present in the date palm leaf extract. This solution was filtered to remove contaminants, first through a cloth and then with Whatman filter paper No. 1. Gelatin (about 20 g) was added to the solution to refine the solution and form a colloidal solution. The refined solution was then freeze dried at −80° C. and 0.3 mbar. The resulting powder containing the co-pigmented anthocyanin complex was stored for further analysis.

Example 2

Analysis of Co-Pigmented Anthocyanin Complex

The co-pigmented anthocyanin complex synthesized according to Example 1 was analyzed in order to confirm its composition.

Gradient reversed-phase HPLC with absorbance detection and MS analysis was used to rapidly identify the main anthocyanins in date palm leaf extracts. Identification was carried out by studying mass spectral data and UV scans, and referring to previous published studies.

Figure 1:
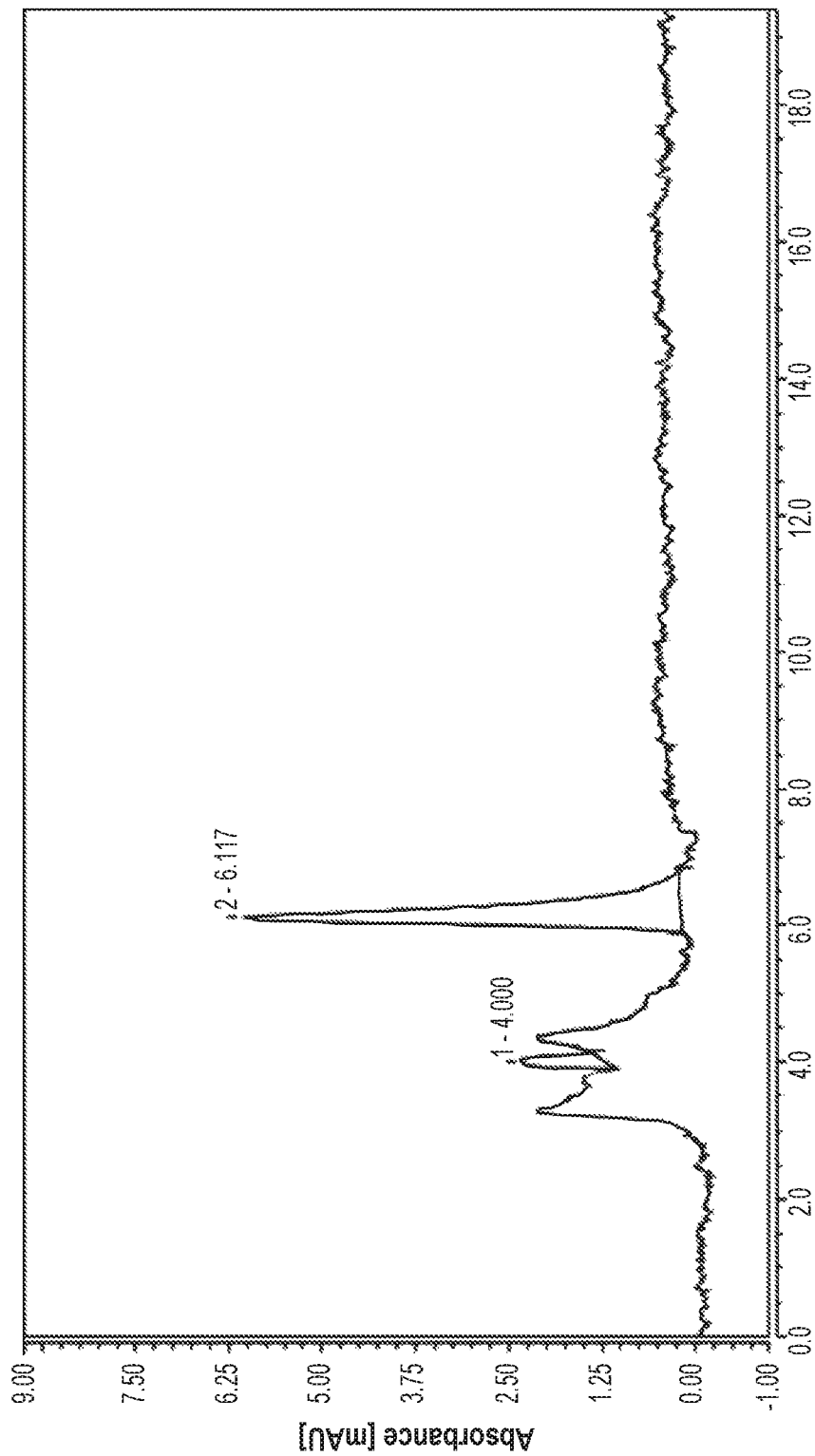
FIG. 1 is the gradient reversed-phase HPLC chromatogram of the anthocyanin synthesized from date palm.
Figure 2:
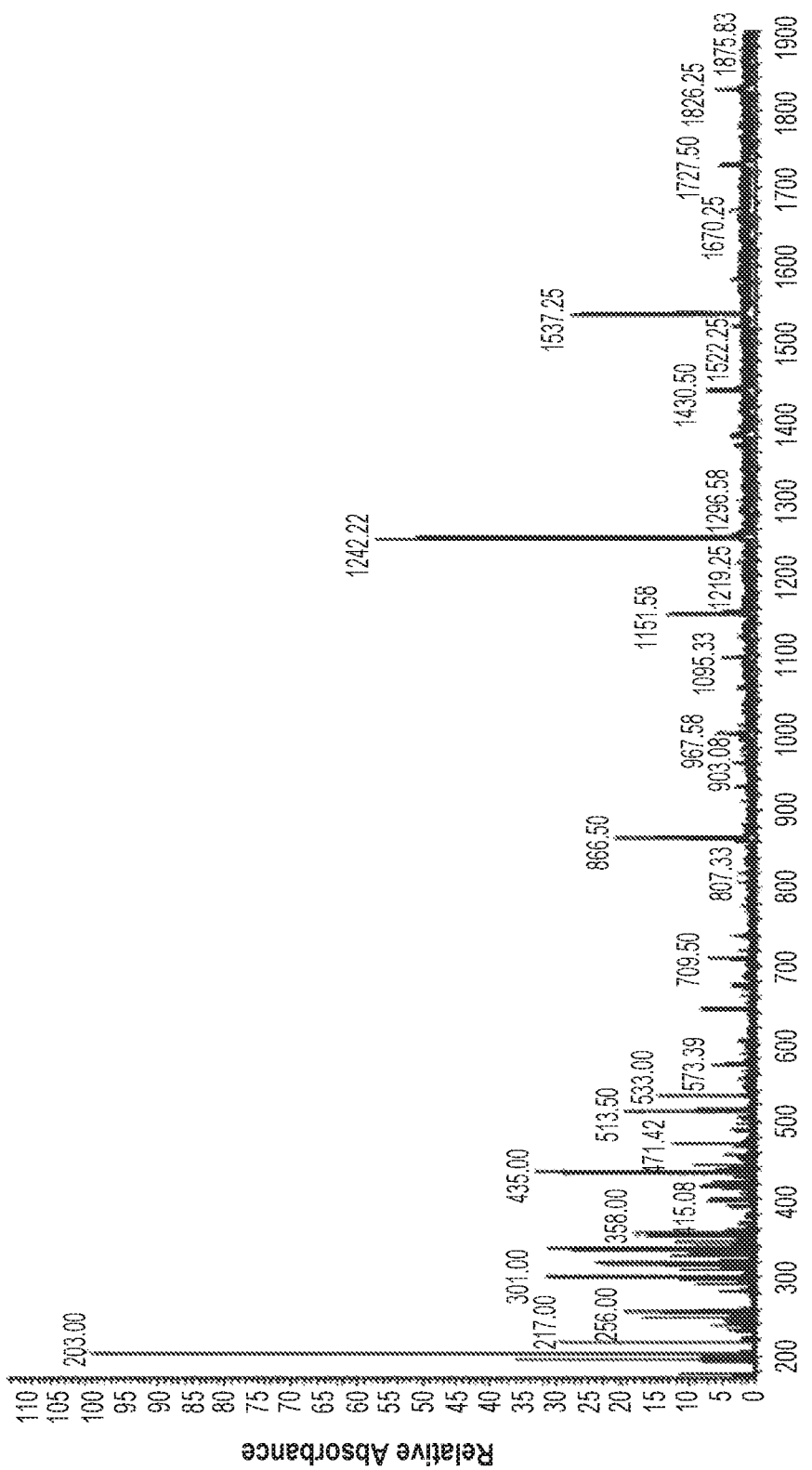
FIG. 2 is the mass spectrum of the anthocyanin synthesized from date palm.
Figure 3:
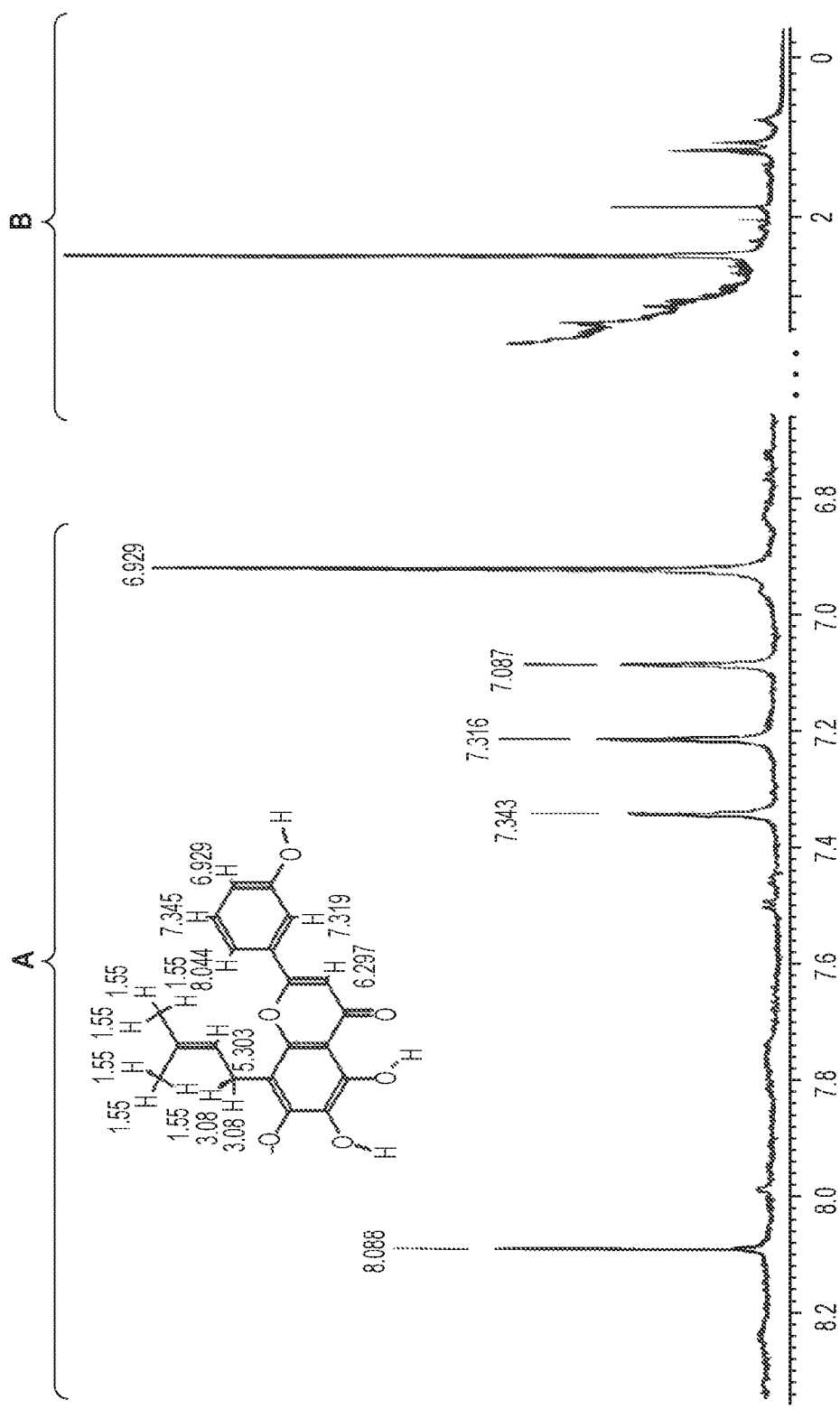
FIG. 3 is the $^1$H NMR spectrum of the anthocyanin synthesized from date palm, showing the aromatic and aliphatic regions of the spectrum.

The HPLC chromatogram of the co-pigmented anthocyanin complex is shown in FIG. 1, and the atmospheric pressure ionization-electron spray mass spectrum (analyzed in positive ion mode) is shown in FIG. 2. The MS fragmentation ions at m/z showed main peaks (M-H)$^+$ at 301.00, 355.00, 435.00, 513.50, 645.60, 865.50, 997.58, 115.58, 1249.33, 1439.50, 1537.25, 1727.50, and 1826.25 Da. The mass spectral data of the co-pigmented anthocyanin complex give a molecular formula of $C_{93}H_{83}O_{39}$. Notably, as there are several anthocyanin aglycones with similar mass and potentially similar fragmentation patterns, the aglycone identity of the co-pigmented anthocyanin complex cannot be guaranteed based on mass spectral fragmentation patterns alone, but the formula of compound 1, shown above, suggests the predicted structure of the co-pigmented anthocyanin complex:

The one-dimensional $^1$H and $^{13}$C NMR spectra of the co-pigmented anthocyanin complex were recorded with a Bruker NMR Avance spectrometer operating at 400 MHz for $^1$H and 75 MHz for $^{13}$C. Samples were dissolved in dimethyl sulfoxide-d6 (DMSO-d6) as a solvent. The resulting $^1$H NMR spectrum is shown in FIG. 3.

In the proton spectrum, peaks were assigned at δ shift (ppm) 8.088, 7.343, 7.216, 7.087, 6.92, 5.51, 2.49, 2.331, 2.042, 1.87, 1.187, 1.16, and 0.78. In the $^{13}$C spectrum, peaks were assigned at 191.21, 189.55, 180.80, 175.12, 171.885, 170.443, 163.88, 161.29, 155.22, 118.71, 85.18, 80.48, 76.78, 75.92, 74.32, 73.03, 68.5, 66.81, 66.50, 66.80, 64.32, 63.01, 62.08, 61.6, 39.83, 39.42, 38.79, 38.62, and 38.57.

The major portions of the $^1$H NMR spectrum appear as continuous distributions of resolved signals (see FIG. 3), suggesting the presence of a pure substance. The bulk of the total organic hydrogen atoms can be divided into five main categories: (1) H—C, aliphatic protons in extended alkyl chains (0.8-2.0 ppm); (2) HC—C=, aliphatic protons attached to carbon atoms adjacent to carbonyl or aromatic groups (2.0-30 ppm); (3) H—C—O, protons attached to carbon atoms singly bonded to oxygen (3.3-5.0 ppm); (4) Ar—H; aromatic portions (6.5-8.5 ppm); and (5) O—H phenolic (4-10 ppm). Numerous signals can be classified and assigned after the $^1$H and $^{13}$C NMR analysis. Some internal composition of the aliphatic moieties ($CH_3$ signals) resonate at $\delta^1$H of 0.8-0.9. A large number of —$CH_2$— signals resonate at $\delta^1$H of 1.2-1.4 ppm confirmed by IR band at 1440 $cm^{-1}$. The peak at $\delta^1$H 2 ppm corresponds to the chemical shift of methylene protons —$CH_2$—(—$CH_2$—C=C) and the aromatic cycle in the form of —$CH_2$—Ar can also correspond to $CH_3$—C=O. The $\delta^1$H of 2.49-2.51 ppm corresponds to (—$CH_2$—Ar) (carbons $\delta^{13}$C 38.79 ppm), the $\delta^1$H of 3.5-4 ppm assigned to $CH_2$—OH can be attributed to asymmetric polyphenols or the CHOH of flavan-3-ol ($\delta^{13}$C 50-80 ppm). There is also a notable absence of $CH_3O$— in the form of a singlet in this region. This is further confirmed by the absence of δ $CH_3O$— towards 55 ppm. Thus, the values of the chemical shift understood in the interval of $\delta^1$H of 4.52-5.6 ppm indicate the presence of olefinic protons of the unsaturated fatty compounds with allylic hydroxyl group (caffeic acid-type). The wide range of $^1$H NMR chemical shift of the signals attributed to aromatic protons suggests the appearance of aromatic rings or substituted phenols (6.5-7 ppm); and benzoic acid or esters and flavonoids and chalcones (>7 ppm).

The $^{13}$C NMR of the co-pigmented anthocyanin complex shows a large number of signals spreading over a wide range of chemical shifts. The spectrum appears complicated, but can be divided into four spectral regions. The regions identified are as follows: (1) aliphatic carbons (10-50 ppm); (2) alkyl carbons (55-80 ppm); (3) olefinic and aromatic carbons (115-140 ppm); and (4) carbonyl carbons (140-176 ppm). The first region, ranging from $\delta^{13}$C with the major signal at $\delta^{13}$C of 38.67-40.68 ppm is characteristic of DMSO-d6 as solvent. The second region from 59.88 to 76 ppm involves resonances of the secondary and tertiary aliphatic carbons oxygenated, which appear to be present in a great quantity (an intense signal was observed at 1114 $cm^{-1}$) in the form of alcohols, ethers (acyclic or cyclic) or esters. The signals of olefinic carbons and aromatic carbons appear in the third region between 115.37 ppm and 133.89 ppm. A few signals of quaternary carbons appear upwardly between 119-136 ppm. The fourth region from 140 to 176 ppm comprises signals of carbonyl carbons, such as quaternary carbons related to heteroatoms (Car-OH, C=O acidic, C=O ketonic normal or combined, or the C=O in the form of esters). The C=O of the carboxylic acids can be found in the region of $\delta^{13}$C of 170.4-170.91 ppm, but can also overlap with other ketonic functions (flavonoids, esters, and the like).

Figure 4:
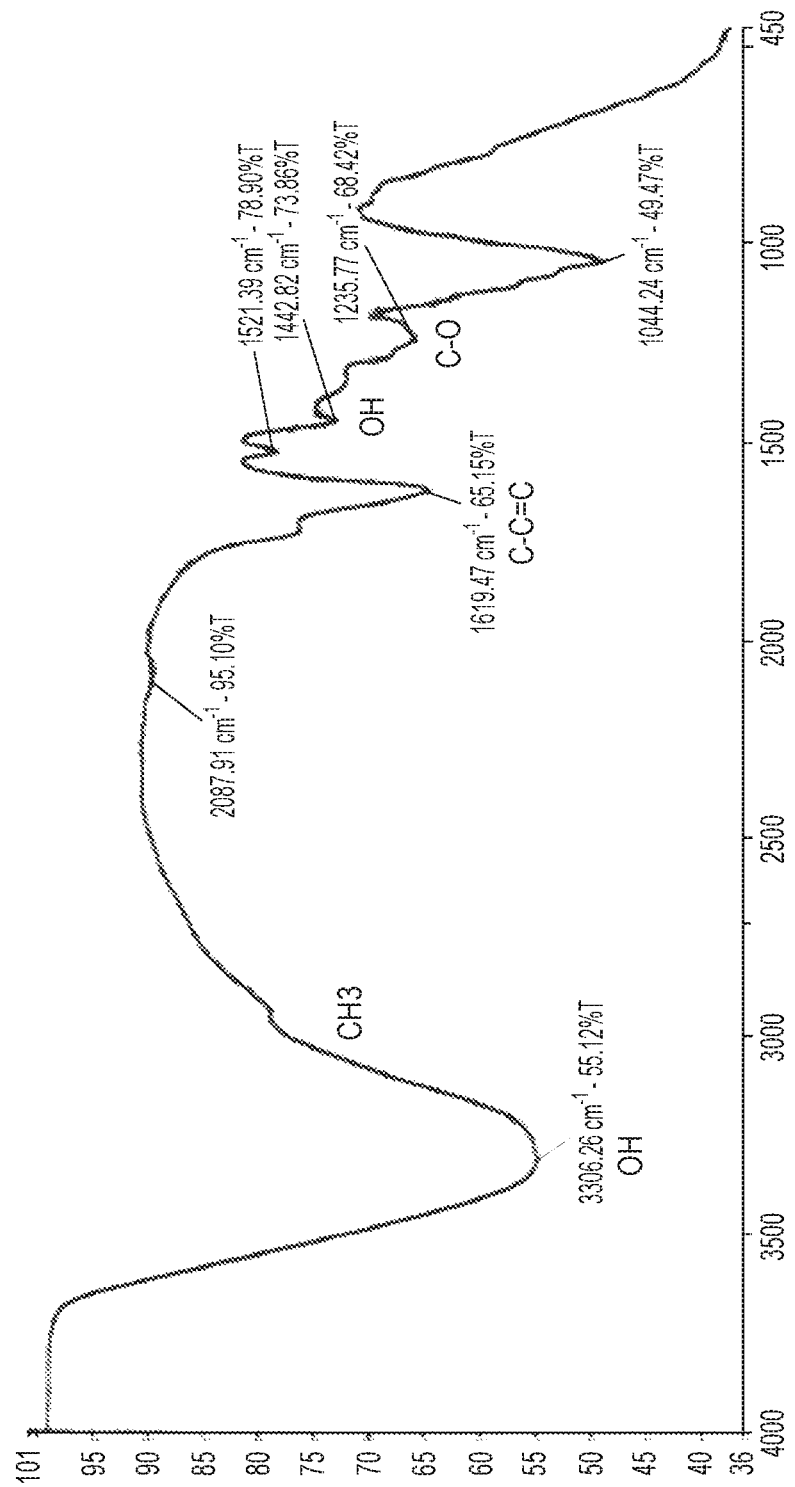
FIG. 4 is the FT-IR spectrum of the anthocyanin synthesized from date palm.

A Fourier Transform Infrared (FT-IR) Spectroscopic Analysis of the co-pigmented anthocyanin complex was performed using a lyophilized sample of the anthocyanin complex. The FT-IR spectra (see FIG. 4) showed a strong signal corresponding to a C—C=C aromatic group vibrational frequency (1618-1645 $cm^{-1}$). At 795-825 $cm^{-1}$, a weak absorption band was observed corresponding to the aromatic C—H bond out of plane flexion movement. A wide band from OH groups was observed in the range of 3222-3310 $cm^{-1}$, while the typical vibrational frequency from C—O bond stretching movement was observed at 1233-1224 $cm^{-1}$. These results are indicative of the presence of phenolic compounds in the molecular structure of the co-pigmented anthocyanin complex.

Figure 5:
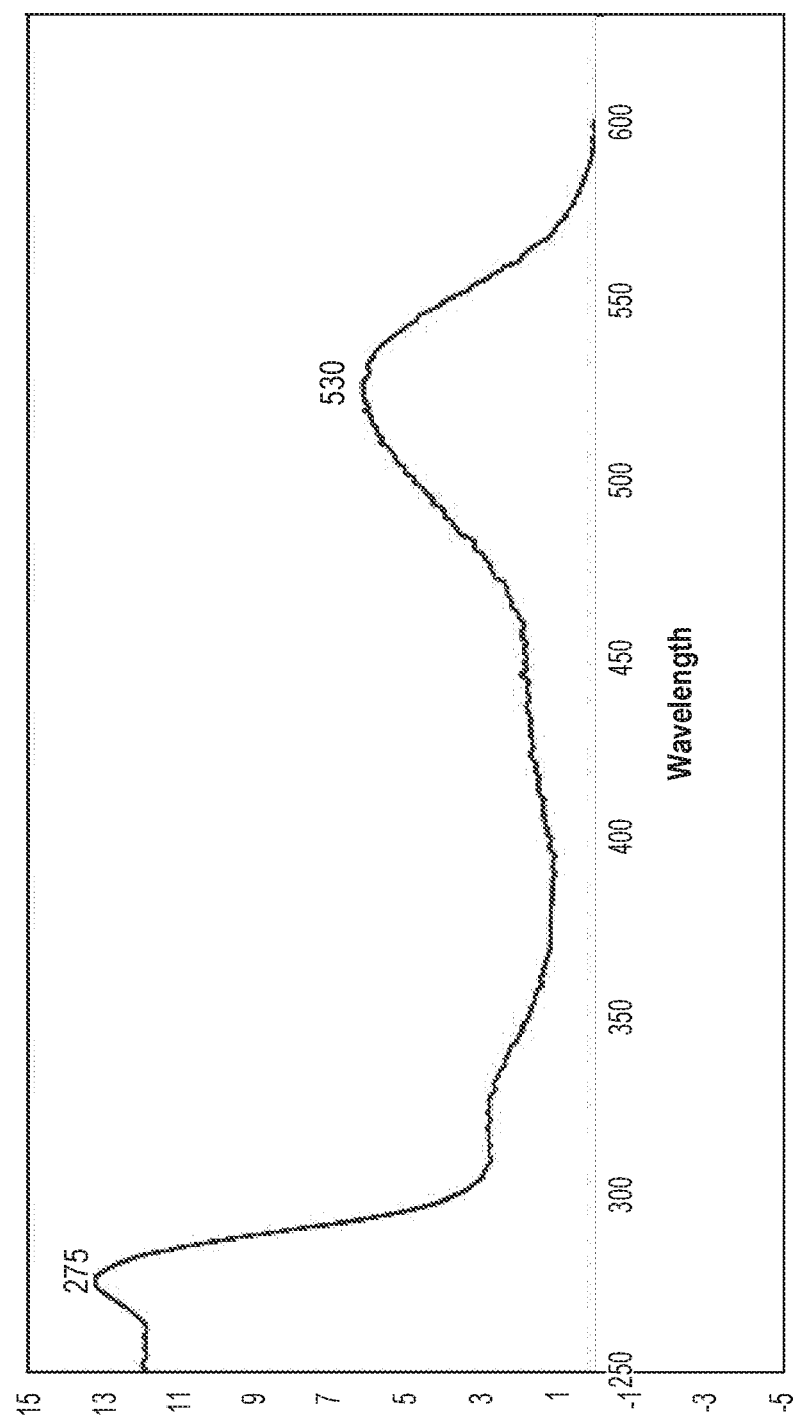
FIG. 5 is the UV-Vis spectrum of the anthocyanin synthesized from date palm.

A UV scan of the co-pigmented anthocyanin complex produced a UV-Visible absorption spectrum (see FIG. 5) recorded between 200 and 600 nm. This spectrophotometric analysis shows maximum absorption bands around 275 nm and 530 nm. Taking into account that anthocyanins display two distinct absorption bands, one in the UV-region (260-280 nm) and another in the visible region (490-550 nm), these results confirm the presence of anthocyanins in the co-pigmented anthocyanin complex.

Example 3

Antioxidant Activity of the Co-Pigmented Anthocyanin Complex

Figure 6A:
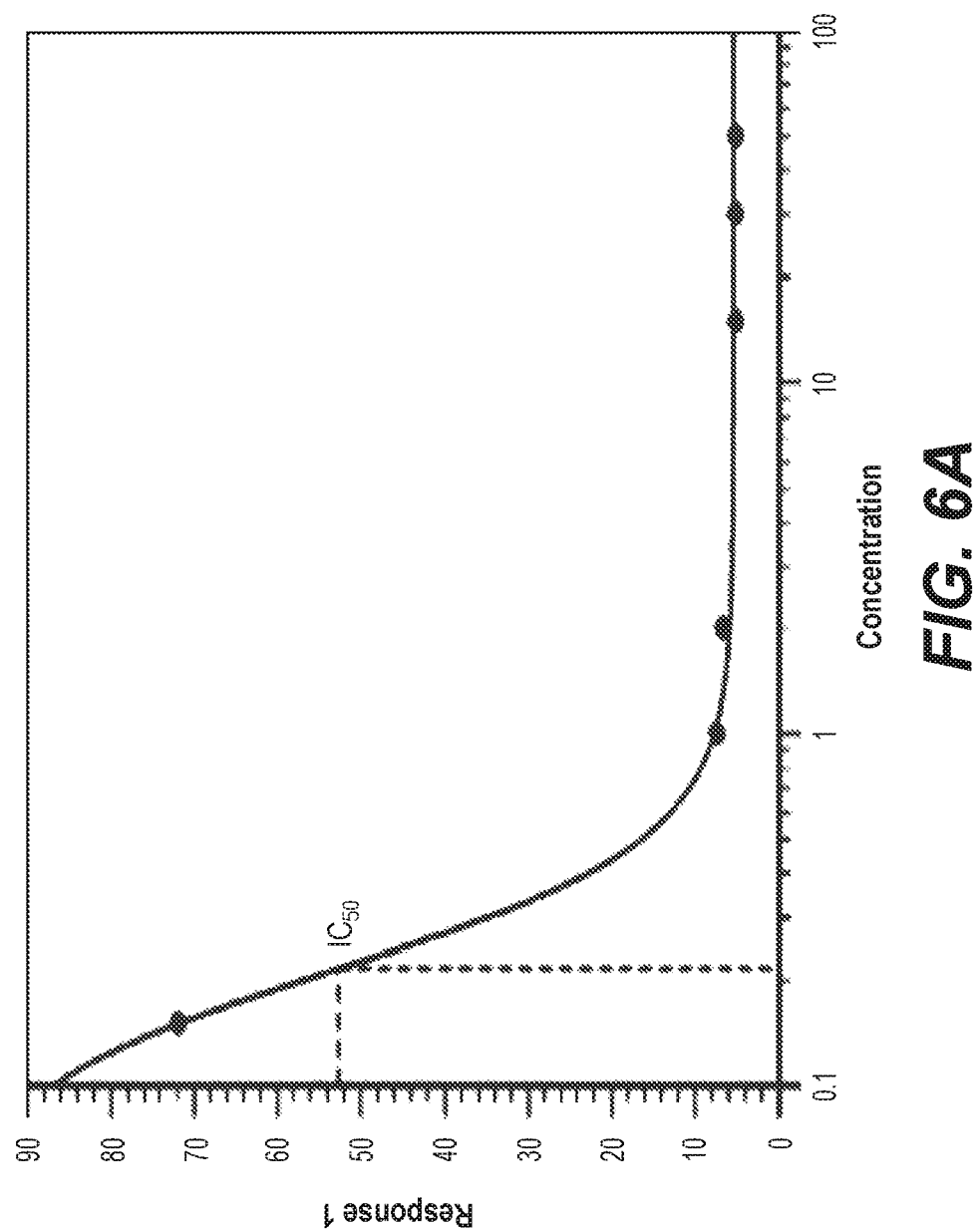
FIG. 6A is a plot of the reaction kinetics of Trolox against DPPH free radical.
Figure 6C:
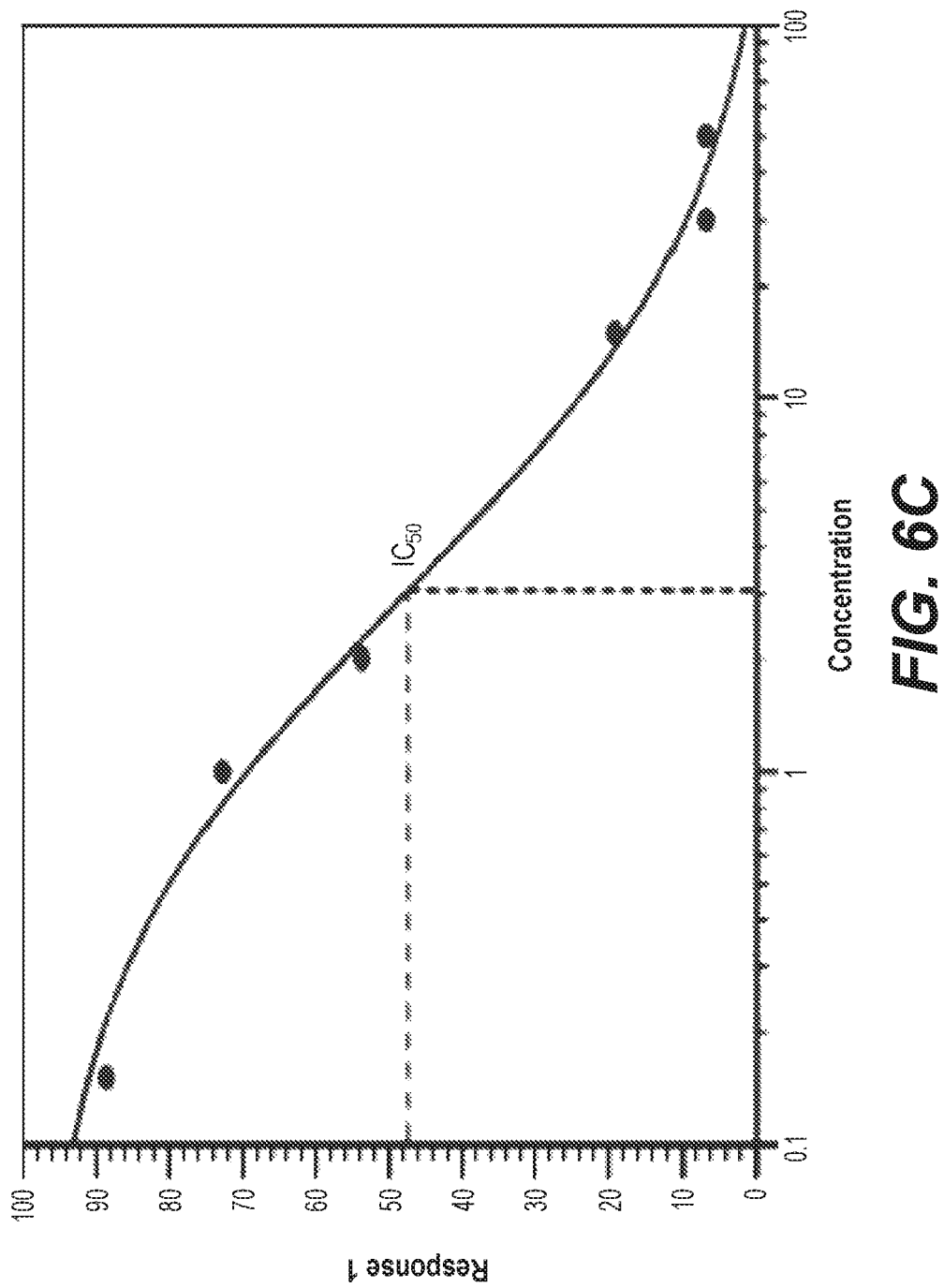
FIG. 6C is a plot of the reaction kinetics of ascorbic acid against DPPH free radical.

Antioxidant activity of the co-pigmented anthocyanin complex was assessed using DPPH as a free radical according to the Brand-Williams method. Activity of the co-pigmented anthocyanin complex was compared with two known antioxidants, ascorbic acid and Trolox. Concentrations tested are expressed as moles of antioxidant per mole DPPH. Briefly, an antioxidant solution in methanol (0.1 ml) was added to 3.9 ml of a $6\times10^{-5}$ mol/L methanol DPPH* solution. The decrease in absorbance was determined at 515 nm at 0 min, 1 min, and every 15 min until the reaction reached a plateau. The extract initial DPPH* concentration (CDPPH) in the reaction medium was calculated from a calibration curve with the equation $Abs_{515\ nm}=0.0765\times$ (CDPPH)+0.1118 as determined by linear regression ($R2=0.9994$). For each antioxidant concentration tested, the reaction kinetics were plotted (see FIGS. 6A-6C). From these graphs, the percentage of DPPH* remaining at the steady state was determined, and the values were transferred onto another graph showing percentage of residual DPPH* at the steady state as a function of the molar ratio of antioxidant to DPPH*. Antiradical activity was defined as the amount of antioxidant necessary to decrease the initial DPPH* concentration by 50% (Efficient Concentration=$EC_{50}$ (mol/L)). The results were analyzed in terms of antiradical power (ARP), with a larger ARP indicating a more efficient antioxidant (ARP=$I/EC_{50}$ AO/(mol/L) DPPH*).

Both the co-pigmented anthocyanin complex and Trolox reacted rapidly with DPPH*, reaching a steady state in less than a minute, while ascorbic acid was intermediate, reaching a steady state after approximately 30 minutes. The ARP of the co-pigmented anthocyanin complex ($IC_{50}$=0.196, ARP=5.05) was slightly higher than that of Trolox (ARP=4.65), and both the co-pigmented anthocyanin complex and Trolox were higher than ascorbic acid ($IC_{50}$=3.031, ARP=0.329).

It is to be understood that the anthocyanin synthesized from date palm is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of synthesizing a co-pigmented anthocyanin complex comprising the steps of:

grinding leaves of date palms (*Phoenix dactylifera*) to obtain about 500 g of powdered date palm leaves;

boiling the powdered date palm leaves in an acidic aqueous extraction solvent to obtain a red extraction mixture, wherein the acidic aqueous extraction solvent consists of about 1.08% hydrochloric acid (wt./vol.) in water, filtering the red extraction mixture to obtain a filtrate;

adding gelatin to the filtrate to obtain a colloidal solution; and freeze-drying the colloidal solution at −80° C. and 0.3 mbar pressure to obtain the co-pigmented anthocyanin as a dry powder, wherein the co-pigmented anthocyanin has the following structural formula:

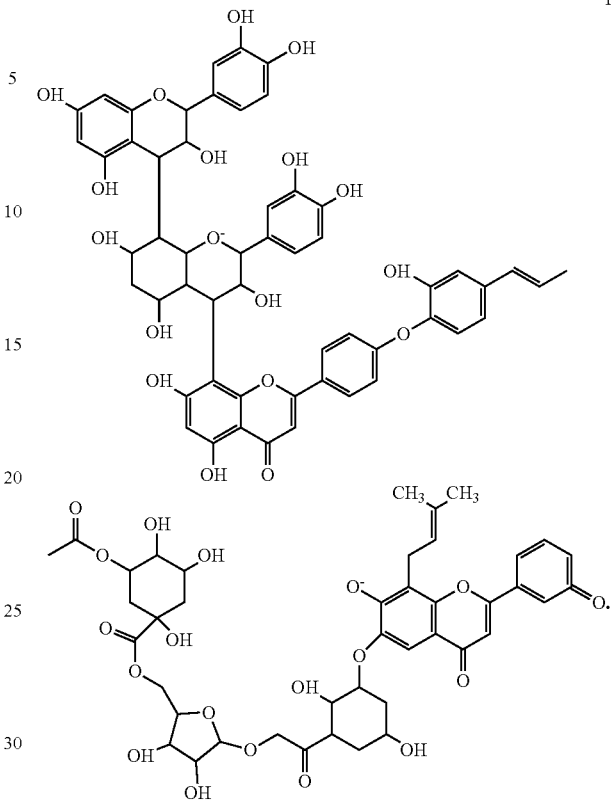

2. The method of claim 1, wherein adding gelatin to the filtrate comprises adding about 20 g of gelatin to about 3 liters of filtrate.

* * * * *